(12) United States Patent
Gohmann et al.

(10) Patent No.: US 9,915,610 B2
(45) Date of Patent: Mar. 13, 2018

(54) SENSOR DEVICE FOR DETERMINING AMBIENT CONDITIONS OF A VEHICLE, IN PARTICULAR OF A MOTOR VEHICLE AND METHOD FOR DETERMINING THE POSITION OF THE SUN

(71) Applicant: Hella KGaA Hueck & Co., Lippstadt (DE)

(72) Inventors: Alexander Gohmann, Bremen (DE); Bastian Kanning, Bremen (DE)

(73) Assignee: Hella KGAA Hueck & Co., Lippstadt (DE)

( * ) Notice: Subject to any disclaimer, the term of this patent is extended or adjusted under 35 U.S.C. 154(b) by 0 days.

(21) Appl. No.: 15/291,678

(22) Filed: Oct. 12, 2016

(65) Prior Publication Data
US 2017/0102327 A1  Apr. 13, 2017

(51) Int. Cl.
G01N 21/55 (2014.01)
B60S 1/08 (2006.01)
G01J 1/42 (2006.01)
G01J 1/02 (2006.01)
G01N 21/552 (2014.01)
G01S 3/783 (2006.01)

(52) U.S. Cl.
CPC .......... G01N 21/552 (2013.01); B60S 1/0833 (2013.01); G01J 1/0242 (2013.01); G01J 1/4204 (2013.01); G01J 1/4228 (2013.01); G01S 3/783 (2013.01); G01N 2201/1244 (2013.01)

(58) Field of Classification Search
CPC ..... B60S 1/0833; G01J 1/4204; G01N 21/552
See application file for complete search history.

(56) References Cited

U.S. PATENT DOCUMENTS

| 8,434,359 B2 | 5/2013 | Niemann et al. | |
| 2012/0006110 A1* | 1/2012 | Niemann | B60S 1/087 73/170.17 |

FOREIGN PATENT DOCUMENTS

| DE | 101 47 176 A1 | 4/2003 | |
| DE | 10 2004 055 060 A1 | 5/2006 | |
| DE | 10 2008 054 640 A1 | 6/2010 | |
| DE | 102008054640 A1 * | 6/2010 | ................ G01J 5/08 |
| DE | 10 2009 007 521 B4 | 6/2011 | |
| DE | 10 2010 026 562 A1 | 1/2012 | |

(Continued)

*Primary Examiner* — Mark R Gaworecki
(74) *Attorney, Agent, or Firm* — Muncy, Geissler, Olds & Lowe, P.C.

(57) ABSTRACT

In a sensor device for determining ambient conditions of a vehicle, in particular a motor vehicle, comprising at least one transmitter for emitting electromagnetic radiation, in particular infrared radiation, comprising at least three receivers for receiving electromagnetic radiation, in particular infrared radiation, wherein at least one transmitter is assigned to at least one receiver for determining precipitation on at least one glass surface, in particular the windscreen of the motor vehicle, and wherein at least three receivers are aligned for receiving electromagnetic radiation from different angular regions, it is provided as essential to the invention that the spatial receiving regions of at least one first and at least one second receiver are aligned substantially horizontally, that the spatial receiving region of at least one third receiver is aligned substantially upwards.

17 Claims, 1 Drawing Sheet

(56) References Cited

FOREIGN PATENT DOCUMENTS

EP 1 514 750 A2 3/2005
EP 1 935 681 A2 6/2008

* cited by examiner

SENSOR DEVICE FOR DETERMINING AMBIENT CONDITIONS OF A VEHICLE, IN PARTICULAR OF A MOTOR VEHICLE AND METHOD FOR DETERMINING THE POSITION OF THE SUN

BACKGROUND OF THE INVENTION

Field of the Invention

The invention relates to a sensor device for determining ambient conditions of a vehicle, in particular a motor vehicle, comprising at least one transmitter for emitting electromagnetic radiation, in particular infrared radiation, comprising at least three receivers for receiving electromagnetic radiation, in particular infrared radiation, wherein at least two receivers are each assigned to one transmitter for determining precipitation on at least one glass surface, in particular the windscreen of a motor vehicle and wherein at least three receivers are aligned for receiving electromagnetic radiation at different angular regions. The invention further relates to a vehicle having a sensor device according to the invention and a method for determining the position of the sun using a sensor device according to the invention.

Brief Description of the Related Art

Methods and devices for determining ambient conditions are used in many vehicles. The ambient conditions can, for example, comprise weather influences such as the wetting state of the windscreen or the position of the sun. Optical sensor devices, for example can be used to determine the wetting state of the windscreen, in which for example, an infrared signal is coupled into the windscreen and after a defined transit distance of the infrared radiation in the windscreen, it can be determined by means of the coupled-out component of the signal how great is the proportion of total reflections in the windscreen. The proportion of total reflections is here influenced by the wetting of the windscreen, for example, with water. In addition to the wetting state of the windscreen, the position of the sun relative to the vehicle is an important parameter since the position of the sun can be incorporated as a parameter in control programs for air-conditioning systems for example. In many cases, combined rain-light sensors can be used to determine the parameters by using dedicated receivers for the illumination state in addition to the transmitters and receivers for determining rain.

For example DE 10 2009 007 521 B4 describes a method for determining the position of the sun for an air-conditioning system of a motor vehicle. Here solar radiation sensors are used of which one is inclined to the right by a certain angle with respect to the vehicle longitudinal direction and the other is inclined to the left by a certain angle. The angle of the position of the sun with respect to the vehicle longitudinal direction and the intensity of the solar irradiation can be determined by means of the solar radiation sensors. During a rotation of the sensor about a vertical axis, the intensity of the solar irradiation is determined multiple times by the left and the right sensor and the normalized difference is calculated from the intensity values. The elevation of the sun is determined from a stored elevation characteristic of the sensor for the determined normalized difference. For the determined elevation of the sun and the current normalized difference, the azimuth angle is determined from the stored elevation characteristic of the sensor.

A disadvantage of the known devices and methods is that solar position sensors provided especially for this purpose must be used. These additional sensors increase the number of components required and increase the costs of the device.

SUMMARY OF THE INVENTION

The invention is based on the object of providing a sensor device of the type mentioned initially in which no sensor elements provided specifically for determining the position of the sun are used.

In the a sensor device for determining ambient conditions of a vehicle, in particular a motor vehicle, comprising at least two transmitters for emitting electromagnetic radiation, in particular infrared radiation, comprising at least three receivers for receiving electromagnetic radiation, in particular infrared radiation, wherein at least one transmitter is assigned to at least one receiver for determining precipitation on at least one glass surface, in particular the windscreen of a motor vehicle and wherein at least three receivers are configured for receiving electromagnetic radiation from different angular regions it is essential to the invention that the spatial receiving regions of at least one first and one second receiver are aligned substantially horizontally, that the spatial receiving region of at least one third receiver is aligned substantially upwards. The sensor device has at least three receivers for electromagnetic radiation, in particular for infrared radiation. The receivers can in particular be photodiodes. The spatial receiving regions, i.e. the spatial angular ranges from which the receivers can detect radiation from two receivers, are aligned horizontally to different sides. In particular, the receivers can be disposed on different sides of a vehicle longitudinal axis, in particular the vehicle central axis. The regions disposed laterally adjacent to the vehicle central axis are the driver region and the passenger region. Preferably the sensor device is disposed on the windscreen of a motor vehicle. At least the first and the second receivers are assigned transmitters for emitting infrared radiation. Infrared radiation can be coupled into the windscreen by a transmitter. As a result of total reflections inside the glass body of the windscreen, the infrared radiation is relayed in the windscreen. A wetting of the windscreen, for example, with rain water leads to a reduction in the proportion of total reflections in the windscreen, i.e. to a partial coupling-out of the infrared radiation from the windscreen. After a defined test distance along the windscreen, the total-reflection proportion of the infrared radiation can be detected by the receivers. The degree of wetting of the windscreen can be concluded by determining the proportion of the total-reflected infrared radiation. These parameters can be used, for example, for the automatic control of a windscreen wiper system. Two rain measuring sections can be formed between a first receiver and a first transmitter and between a second transmitter and a second receiver. These can be aligned horizontally along the windscreen, i.e. transversely, in particular at right angles to the vehicle longitudinal axis. For example, the first receiver can be aligned facing the passenger side and the second receiver can be aligned facing the driver side. The spatial receiving regions of the two receivers can thus point in different directions. The relevant transmitters are accordingly arranged so that the radiation coupled into the windscreen lies in the receiving region of the relevant receiver. In addition to the first and second receiver, the sensor device has a third receiver. This receiver can also be assigned to a transmitter and thus combined with the transmitter form a measuring section for the precipitation on the windscreen. The third receiver is arranged vertically to the measuring sections between the first and second receiver and the associated transmitters. In particular, in the arrangement of the sensor device on a windscreen, the receiver can be arranged above or below the first and second receiver and the associated transmitters. In particular, the third receiver can be arranged vertically under a transmitter. The spatial receiving region of the third receiver is aligned upwards. In particular the three receivers are thus aligned in different directions. In addition to the formation of three measuring sections to determine the precipitation on the windscreen, the three receivers can also be used to determine the position of the sun. The receivers are configured to detect infrared radiation. This is emitted by the sun so that by detecting infrared radiation from three different directions, the position of the sun can be deduced. Preferably the three receivers, in particular, the photodiodes have identical spectral sensitivities. The receivers each output a radiation intensity value. By comparing and normalizing the three irradiation intensity signals, the current position of the sun can be calculated. By using three receivers which are aligned in different spatial directions, it is possible to determine the wetting state of the windscreen and also the position of the sun. Two receivers are assigned to at least one transmitter. For example, a transmitter can be configured so that the infrared signal coupled into the windscreen by the transmitter can be received by a receiver arranged horizontally to the transmitter and a receiver arranged vertically to the transmitter. Thus two measuring sections for determining the precipitation on the windscreen are formed between the transmitter and the two receivers. Thus, three measuring sections for determining the precipitation on the windscreen can be formed using two transmitters and three receivers.

In a further development of the invention, the maxima of the spatial receiving characteristics of at least two receivers point in opposite directions and the maximum of the spatial receiving characteristic of a third receiver is aligned vertically to the axis of the spatial receiving characteristics of the oppositely directed receivers. The maximum of the spatial receiving characteristic of a receiver designates the solid angle at which the receiver has its maximum sensitivity and thus outputs the highest irradiation intensity value under corresponding illumination. As a result of the arrangement of a first and a second receiver with maxima of the spatial receiving characteristic pointing in opposite direction, incident radiation for example from the region of the driver side and the region of the passenger side of a vehicle can be detected. The maximum of the spatial receiving characteristic of a third receiver can be aligned vertically to the maxima of the spatial receiving characteristics of the first and second receivers. As a result of the vertical alignment of the third receiver to the first and second receivers, infrared radiation can be detected from three different directions. In particular, the passenger side, the driver side and the region facing away from the surface covered by the vehicle, i.e. the upwardly directed region, can be detected. The position of the sun in relation to the motor vehicle can be detected by recording values of the irradiation intensity from three spatial directions.

In a further development of the invention, the receivers have an at least approximately identical spectral sensitivity. In order to be able to calculate the position of the sun from, for example, irradiation intensity values from three different spatial directions, for reasons of comparability or normalizability the receivers must have the same spectral sensitivity so that they output the same irradiation intensity value under the same irradiation.

In a further development of the invention, the sensor device comprises at least one coupling-in element for coupling in the electromagnetic radiation of a transmitter into a glass surface and at least one coupling-out element for coupling out the electromagnetic radiation from a glass surface. The coupling-in elements can in particular be optical components which enable infrared radiation from the transmitter to be introduced into the windscreen of a vehicle. For example, the coupling-in elements can be lens-shaped components which are arranged between the transmitters and the windscreen. The coupling-out elements can also be lens-shaped components which, after the infrared radiation emitted by the transmitter has covered a measuring section in the windscreen, couple out the infrared radiation for detection by a receiver. The coupling-in and coupling-out elements are required for determining precipitation on the windscreen. During the determination of the position of the sun via the receivers, the optical components have no function.

In a vehicle having at least one windscreen and having at least one sensor device according to the invention, it is essential to the invention that the sensor device is disposed on the windscreen, that at least one receiver is aligned facing the driver's side of the vehicle, that at least one receiver is aligned facing the passenger side of the vehicle and that at least one receiver is aligned facing away from the base surface on which the vehicle is moving. The sensor device is disposed on the windscreen. Thereby, a receiver for receiving electromagnetic radiation, in particular infrared radiation, is disposed facing the passenger side. In particular, the receiver can be aligned here such that the maximum of the spatial receiving characteristic is aligned horizontally, i.e. transversely to the vehicle longitudinal axis. A second receiver is preferably disposed such that it is aligned facing the driver side. The maximum of the receiving characteristic, i.e. the angle at which the receiver has its highest sensitivity is also aligned transversely to the vehicle longitudinal axis. Accordingly the transmitters are disposed on the axes of the maxima of the spatial receiving characteristics of the first and second receivers. The transmitters are configured for emitting infrared radiation. Through the transmitters, infrared radiation can be coupled into the windscreen which can be detected at a distance forming the measuring section by the associated receivers. The wetting state of the windscreen can be calculated by means of the proportion of the radiation undergoing total reflection in the windscreen. Preferably a first receiver and a first transmitter are disposed at the same height with reference to the ground on which the vehicle is moving. Also a second transmitter and a second receiver are arranged on a horizontal plane at the same level. For example, another third receiver can be assigned to the second transmitter. This is disposed vertically under the transmitter with reference to the ground along the surface of the windscreen. Preferably the two imaginary connecting lines formed in each case between the transmitter and the two associated receivers span a right angle. Therefore two measuring sections for determining the wetting state of the windscreen are formed between the transmitter and the two receivers. The first two receivers are aligned to the passenger side and to the driver side of the vehicle, preferably on both sides of the vehicle central longitudinal axis. The third receiver is aligned facing away from the ground on which the vehicle is moving. Thus, the third receiver is aligned upwards, i.e. for example facing the sky. The spatial receiving characteristics of the three receivers therefore point in three different directions. In addition to receiving infrared radiation which is coupled out by the transmitters, the receivers can also detect infrared radiation from the ambient light, for example, infrared radiation emitted by the sun. By recording respectively one irradiation intensity value with each of the three receivers, the position of the sun can be deduced. The receivers can therefore be used in this arrangement both for determining the degree of wetting of the windscreen, i.e. as a rain sensor, and also for determining the position of the sun. It is not necessary to use additional components. A reduced list of components and therefore a cost saving compared with the use of separate rain-light sensors is achieved.

In a further development of the invention, the receiver aligned facing away from the base surface is disposed along the surface of the windscreen in relation to the base surface above or below the transmitters. The two receivers aligned to the sides, in particular to the passenger side and to the driver side, are each assigned a transmitter. Preferably a transmitter-receiver pair is disposed on a horizontal axis at a height from the base surface. The connecting lines between a receiver and a transmitter are here arranged transversely to the vehicle longitudinal axis. A third receiver which faces away from the surface covered, i.e. is aligned upwards in the direction of the sky, is aligned above or below the two receiver-emitter pairs directed horizontally to the side when viewed from the base surface. The windscreen of a vehicle is usually inclined contrary to the direction of travel. For example, the upwardly directed receiver can be aligned along the surface of the windscreen further in the direction of the base surface than the two other receiver-transmitter pairs. As a result of this arrangement, an undisturbed transmission of infrared radiation from the surroundings of the vehicle, for example from the sun onto the receiver is achieved. It is therefore possible to receive infrared radiation from three directions using the receivers.

In a method for determining the position of the sun using a sensor device according to the invention, it is provided as essential to the invention that at least one irradiation intensity value of the ambient light is detected in each case by means of at least three receivers, that the maximum value of the detected irradiation intensity values is determined and that the side of the vehicle facing the sun is deduced from the maximum irradiation intensity values. The three receivers of the sensor device are aligned to different directions. Here preferably one receiver is aligned to the passenger side of the vehicle and one receiver is aligned to the driver side of the vehicle, i.e. to both sides of the vehicle central axis and one receiver is aligned facing away from the ground on which the vehicle is moving, i.e. facing the sky. One value of the radiation intensity in each case is determined using these three receivers. In order to ensure a comparability of the irradiation intensity values, the receivers have the same spectral sensitivity. In order to determine the position of the sun from the recorded values of the irradiation intensity, the maximum value of the three recorded irradiation intensity values is determined. By determining which of the three receivers has output the highest irradiation intensity value, the direction from which the sun shines on the vehicle can be deduced.

In a further development of the method, the irradiation intensity values are detected temporally consecutively by the receivers. The receivers are provided both to determine a wetting of the windscreen with a liquid and also to determine the position of the sun. Preferably the irradiation intensity values of the ambient light are detected whilst no determination of the wetting state is made. Whilst the irradiation intensity values of the ambient light are detected by the receivers, no infrared radiation is therefore emitted by the transmitters. The irradiation intensity values are detected temporally consecutively by the three receivers. For example, the irradiation intensity value can initially be determined on the passenger side, then the irradiation intensity value of the driver side is determined and following this, the irradiation intensity value is determined with the upwardly directed receiver. The determined irradiation intensity values can be processed by an evaluation device.

In a further development of the invention, the irradiation intensity values determined with the two substantially horizontally aligned receivers are divided by the determined maximum irradiation intensity value for normalizing, the smaller of the two normalized irradiation intensity values is subtracted from the larger of the two normalized irradiation intensity values, the arc cosine is formed from the result of the subtraction and the arc cosine is assigned to the azimuth angle of the position of the sun. In order to determine the position of the sun, in particular the azimuth angle of the position of the sun, the maximum value of the two horizontally aligned receivers is determined. A normalization of the two irradiation intensity values is made by dividing by the determined maximum value. If the irradiation intensity values of the two receivers are the same, the sun is precisely in the direction of travel. The smaller of the two normalized irradiation intensity values is subtracted from the larger maximum irradiation intensity value which is acquires the value 1 by normalizing. The result of the subtraction corresponds to the adjacent side of the triangle for determining the azimuth whereas the vector of the position of the sun forms the hypotenuse. By forming the inverse function of the cosine, i.e. the arc cosine, the azimuth angle of the position of the sun in relation to the sensor device can be deduced.

In a further development of the method, a vector is determined in each case from the irradiation intensity signals measured with the two substantially horizontally aligned receivers, a sum vector is formed from the two vectors, the magnitude of the resulting sum vector is compared with the signal of the irradiation intensity measured using the substantially upwardly directed receiver, the measured irradiation intensity values are normalized, the smaller of the two normalized irradiation intensity values is subtracted from the larger of the two normalized intensity values, the arc cosine is formed from the result of the subtraction and the arc cosine is assigned to the elevation angle of the position of the sun. Vectors can be determined from the measured signals of the two substantially horizontally aligned receivers. A sum vector can be formed from the two vectors. For determining the elevation angle the magnitude of the sum vector is compared with the signal of the substantially upwardly directed receiver. The maximum value of the irradiation intensity value resulting from the sum vector and the irradiation intensity value measured by the upwardly directed receiver are determined. For the normalization the irradiation intensity values are divided by the maximum irradiation intensity value. The smaller of the two normalized irradiation intensity values is subtracted from the larger of the two normalized irradiation intensity values and the arc cosine is formed from the result of the subtraction. The arc cosine corresponds to the elevation angle of the position of the sun with respect to the sensor device.

BRIEF DESCRIPTION OF THE DRAWING

The invention is explained further with reference to a preferred exemplary embodiment shown in the drawings.

DETAILED DESCRIPTION OF THE PREFERRED EMBODIMENTS

Figure 1:
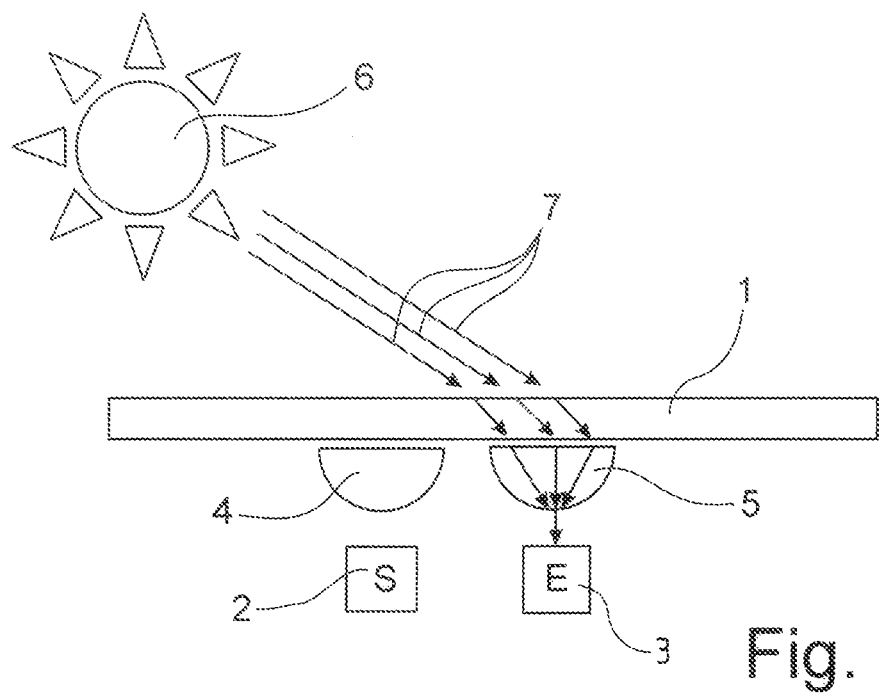
FIG. 1: shows an arrangement of transmitter and receiver for determining an irradiation intensity value and the degree of wetting of a windscreen.

FIG. 1 shows a measuring section for determining the precipitation on a windscreen 1 of a vehicle. The measuring section is constructed from a transmitter 2 and a receiver 3. A coupling-in element 4 is arranged between the transmitter 2 and the windscreen 1 by means of which the infrared radiation emitted by the transmitter 2 can be coupled into the windscreen 1. Accordingly a coupling-out element 5 is disposed between the receiver 5 and the windscreen 1 by means of which the coupled-in infrared radiation is coupled out to the receiver 3. In the windscreen the infrared radiation emitted by the transmitter 2 can be relayed by total reflections. In the case of a wetting of the windscreen 1, for example, with rain water, total reflections do not occur in the windscreen 1 but the infrared radiation is partially coupled out along a measuring section. The receiver 3 can detect how high is the proportion of total reflections in the windscreen 1 or the proportion of coupled-out light from which the wetting state of the windscreen 1 can be deduced. In addition to determining the wetting state, the receiver 3 can be used for determining the position of the sun, The infrared radiation 7 emitted by the sun 6 is detected by the receiver 3. The detection of the infrared radiation 7 emitted by the sun is preferably made whilst no infrared radiation is emitted by the transmitter. By using a plurality of receivers 3 aligned in different directions, it is possible to determine the position of the sun.

Figure 2:
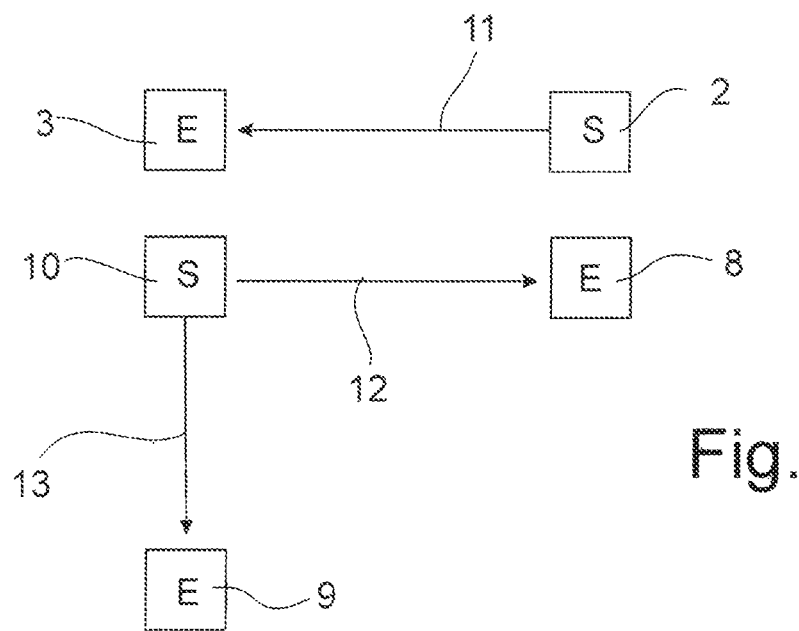
FIG. 2: shows an arrangement of three measuring sections for determining the degree of wetting of a windscreen and the position of the sun.

FIG. 2 shows the arrangement of three measuring sections to determine the position of the sun. Here three receivers 3, 8, 9 are assigned to two transmitters 2, 10. Preferably the arrangement is disposed on the windscreen 1 of a vehicle. Measuring sections in this arrangement are formed between the transmitter 2 and the receiver 3, between the transmitter 10 and the receiver 8 and between the transmitter 10 and the receiver 9. The measuring section 11 arranged between the transmitter 2 and the receiver 3 and the measuring section 12 arranged between the transmitter 10 and the receiver 8 are horizontally aligned. In particular, the measuring sections 11, 12 are aligned transversely to a vehicle longitudinal axis. The receiver 3 is aligned facing the passenger side whilst the receiver 8 is aligned facing the driver side. A measuring section 13 which runs transversely to the measuring sections 11 and 12 is formed between the transmitter 10 and the receiver 9. Along the windscreen 1 the receiver 9 is located underneath the transmitter 10. The receiver 9 is arranged so that it is aligned facing away from the base surface on which the vehicle is moving. As a result of the inclination of the windscreen 1, the upwardly directed receiving field of the receiver 9 is not disturbed by the transmitters 2, 10 or the other receivers 3, 8. As a result of the alignment of the receivers 3, 8 and 9, it is possible to detect infrared radiation from three different directions in relation to the vehicle. As a result of the arrangement of the transmitters and receivers with respect to one another, it is possible to determine a wetting state of the windscreen 1 and also to determine the position of the sun without further components.

All the features mentioned in the preceding description and in the claims can be combined in an arbitrary selection with the features of the independent claims. The disclosure of the invention is thus not restricted to the described or claimed feature combinations but rather all appropriate feature combinations within the scope of the invention should be considered to be disclosed.

The invention claimed is:

1. A sensor device for determining ambient conditions of a vehicle, comprising:
   at least one transmitter for emitting electromagnetic radiation,
   at least three receivers for receiving electromagnetic radiation,
   wherein said at least one transmitter is assigned to at least one receiver of said at least three receivers for determining precipitation on at least one glass surface,
   wherein said at least three receivers are aligned for receiving electromagnetic radiation from different angular regions,
   wherein spatial receiving regions of at least one first and at least one second receiver of said at least three receivers are aligned substantially horizontally, and a spatial receiving region of at least one third receiver of said at least three receivers is aligned substantially upwards and that two receivers are assigned to said at least one transmitter.

2. The sensor device according to claim 1, wherein a maxima of spatial receiving characteristics of at least two receivers of said at least three receivers point in opposite directions and that a maximum of spatial receiving characteristic of a third receiver of said at least three receivers is aligned vertically to the axis of the spatial receiving characteristics of the oppositely directed receivers.

3. The sensor device according to claim 2, wherein the receivers have a substantially identical spectral sensitivity.

4. The sensor device according to claim 2, wherein the sensor device comprises at least one coupling-in element for coupling in the electromagnetic radiation of a transmitter into a glass surface and at least one coupling-out element for coupling out the electromagnetic radiation from a glass surface.

5. The sensor device according to claim 1, wherein the three receivers have a substantially identical spectral sensitivity.

6. The sensor device according to claim 5, wherein the sensor device comprises at least one coupling-in element for coupling in the electromagnetic radiation of a transmitter into a glass surface and at least one coupling-out element for coupling out the electromagnetic radiation from a glass surface.

7. The sensor device according to claim 1, wherein the sensor device comprises at least one coupling-in element for coupling in the electromagnetic radiation of a transmitter into a glass surface and at least one coupling-out element for coupling out the electromagnetic radiation from a glass surface.

8. A vehicle having at least one windscreen and having at least one sensor device according to claim 1, wherein the sensor device is disposed on the windscreen,
   at least one receiver of said at least three receivers is aligned facing the driver's side of the vehicle,
   at least one receiver of said at least three receivers is aligned facing the passenger side of the vehicle, and
   at least one receiver of said at least three receivers is aligned facing away from the base surface on which the vehicle is moving.

9. The vehicle according to claim 8, wherein the at least one receiver aligned facing away from the base surface is disposed along the surface of the windscreen in relation to the base surface above or below the transmitters.

10. The sensor device according to claim 1, wherein the vehicle is a motor vehicle.

11. The sensor device according to claim 1, wherein the electromagnetic radiation is infrared radiation.

12. The sensor device according to claim 1, wherein the glass surface is a windscreen of a motor vehicle.

13. The sensor device according to claim 1, wherein the three receivers are configured to detect infrared radiation by the sun and thereby determine the position of the sun.

14. A method for determining the position of the sun using a sensor device according to the invention, wherein:
at least one irradiation intensity value of the ambient light is detected by means of at least three receivers,
a maximum value of the detected irradiation intensity values is determined,
a side of a vehicle facing the sun is deduced from the maximum irradiation intensity values,
wherein the irradiation intensity values determined with two substantially horizontally aligned receivers of said at least three receivers are divided by the determined maximum irradiation intensity value for normalizing, the smaller of the two normalized irradiation intensity values is subtracted from the larger of the two normalized irradiation intensity values, the arc cosine is formed from the result of the subtraction and the arc cosine is assigned to the azimuth angle of the position of the sun.

15. The method according to claim 14, wherein the irradiation intensity values are detected temporally consecutively by the receivers.

16. The method according to claim 15, wherein a vector is determined from the irradiation intensity signals measured with the two substantially horizontally aligned receivers, a sum vector is formed from the two vectors, the magnitude of the resulting sum vector is compared with the signal of the irradiation intensity measured using a substantially upwardly directed receiver, the measured irradiation intensity values are normalized, the smaller of the two normalized irradiation intensity values is subtracted from the larger of the two normalized intensity values, the arc cosine is formed from the result of the subtraction and the arc cosine is assigned to the elevation angle of the position of the sun.

17. The method according to claim 14, wherein a vector is determined from the irradiation intensity signals measured with the two substantially horizontally aligned receivers, a sum vector is formed from the two vectors, the magnitude of the resulting sum vector is compared with the signal of the irradiation intensity measured using a substantially upwardly directed receiver, the measured irradiation intensity values are normalized, the smaller of the two normalized irradiation intensity values is subtracted from the larger of the two normalized intensity values, the arc cosine is formed from the result of the subtraction and the arc cosine is assigned to the elevation angle of the position of the sun.

* * * * *